US011510860B2

(12) United States Patent
Douezan et al.

(10) Patent No.: US 11,510,860 B2
(45) Date of Patent: Nov. 29, 2022

(54) COMPOSITION COMPRISING A UV-SCREENING AGENT, AN ACRYLIC POLYMER AND A FATTY ACID ESTER OF DEXTRIN

(71) Applicant: L'OREAL, Paris (FR)

(72) Inventors: Stéphane Douezan, Chevilly la Rue (FR); Alexandra Batista, Chevilly la Rue (FR)

(73) Assignee: L'OREAL, Paris (FR)

( * ) Notice: Subject to any disclaimer, the term of this patent is extended or adjusted under 35 U.S.C. 154(b) by 242 days.

(21) Appl. No.: 16/763,391

(22) PCT Filed: Nov. 15, 2018

(86) PCT No.: PCT/EP2018/081473
§ 371 (c)(1),
(2) Date: May 12, 2020

(87) PCT Pub. No.: WO2019/096958
PCT Pub. Date: May 23, 2019

(65) Prior Publication Data
US 2020/0315944 A1    Oct. 8, 2020

(30) Foreign Application Priority Data
Nov. 15, 2017    (FR) ...................... 1760730

(51) Int. Cl.
A61K 8/73      (2006.01)
A61K 8/37      (2006.01)
A61K 8/81      (2006.01)
A61Q 19/08     (2006.01)
A61Q 17/04     (2006.01)

(52) U.S. Cl.
CPC ............... *A61K 8/738* (2013.01); *A61K 8/37* (2013.01); *A61K 8/8152* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| 4,128,635 | A | 12/1978 | Hase et al. |
| 2004/0005279 | A1 | 1/2004 | Lorant et al. |
| 2007/0264204 | A1 | 11/2007 | Noor et al. |
| 2009/0105353 | A1 | 4/2009 | Lorant |
| 2010/0202985 | A1* | 8/2010 | SenGupta ............... A61K 8/27 424/59 |
| 2011/0097288 | A1 | 4/2011 | Janssen |
| 2012/0244202 | A1 | 9/2012 | Simonnet |
| 2013/0052148 | A1 | 2/2013 | Chavan |
| 2017/0348219 | A1* | 12/2017 | Uyama ............... A61K 8/8152 |

FOREIGN PATENT DOCUMENTS

| DE | 26 08 875 A1 | 9/1977 | |
| EP | 1 386 600 A1 | 2/2004 | |
| EP | 1386600 A1 * | 2/2004 | ............. A61K 8/042 |
| EP | 2 039 339 A2 | 3/2009 | |
| EP | 3 235 839 A1 | 10/2017 | |
| FR | 2 843 020 A1 | 2/2004 | |
| FR | 3 046 076 A1 | 6/2017 | |
| GB | 1 560 428 A | 2/1980 | |
| JP | 52 108030 A | 9/1977 | |
| JP | 2009 120493 A | 6/2009 | |
| JP | 2009 536949 A | 10/2009 | |
| JP | 2012 144580 A | 8/2012 | |
| JP | 2013 520464 A | 6/2013 | |
| JP | 2014-185137 A | 10/2014 | |
| JP | 2015-131767 A | 7/2015 | |
| JP | 2015-164970 A | 9/2015 | |
| WO | WO 2007/133720 A2 | 11/2007 | |
| WO | WO 2011 104228 A1 | 9/2011 | |
| WO | WO-2016098456 A1 * | 6/2016 | ............. A61K 8/042 |

OTHER PUBLICATIONS

JPO English abstract for JP 2015-131767 (Sase et al.) (Year: 2015).
DERWENT English abstract for JP 2012-144580 (Sekiguchi et al.) (Year: 2012).
Machine-assisted English translation for JP 2015-131767 (Sase et al.) (Year: 2015).
Machine-assisted English translation for JP 2012-144580 (Sekiguchi et al.) (Year: 2012).

* cited by examiner

*Primary Examiner* — Dominic Lazaro
(74) *Attorney, Agent, or Firm* — Polsinelli PC

(57) ABSTRACT

The present invention relates to a composition, especially a cosmetic, in particular photoprotective, composition, comprising at least: —one or more particular acrylic polymers —one or more fatty acid esters of dextrin, and —one or more UV-screening agents.

22 Claims, No Drawings

COMPOSITION COMPRISING A UV-SCREENING AGENT, AN ACRYLIC POLYMER AND A FATTY ACID ESTER OF DEXTRIN

CROSS REFERENCE TO RELATED APPLICATIONS

This application is a National Phase filing under 35 U.S.C. § 371 of PCT/EP2018/081473 filed on 15 Nov. 2018; which application in turn claims priority to Application No. 1760730 filed in France on 15 Nov. 2017. The entire contents of each application are hereby incorporated by reference.

The invention relates to a composition, especially a cosmetic, and in particular photoprotective, composition, and to a process for treating keratin materials, in particular the skin and skin appendages, using said composition.

It is known that light radiation with wavelengths of between 280 and 400 nm makes it possible to brown the human epidermis. However, rays with wavelengths more particularly between 280 and 320 nm, known as UV-B rays, cause skin erythema and burns which can be detrimental to the development of a natural tan.

For these reasons, and also for aesthetic reasons, there is constant demand for means for controlling this natural tanning in order to control the colour of the skin; this UV-B radiation should thus be screened out.

It is also known that UV-A rays, with wavelengths of between 320 and 400 nm, and which cause browning of the skin, are liable to induce adverse changes therein, in particular in the case of sensitive skin or skin that is continually exposed to solar radiation. UV-A rays cause in particular a loss in the elasticity of the skin and the appearance of wrinkles, resulting in premature skin ageing.

It is therefore desirable also to screen out UV-A radiation.

Many photoprotective compositions have been proposed to date for protecting against the effects induced by UVA and/or UVB radiation. These compositions generally contain organic or mineral screening agents, more particularly mixtures of organic liposoluble screening agents and/or of water-soluble screening agents, combined with metal oxide pigments such as titanium dioxide or zinc oxide. These inorganic particles make it possible to increase the sun protection, which reduces the amount of organic screening agents and thus improves the cosmeticity of the formulations.

While mineral screening agents such as titanium dioxide or zinc oxide are widely used in cosmetics for their UV-absorbing properties, they cause, however, whitening when they are applied to the skin, which is not attractive.

Dextrin esters are in particular known as oil thickeners.

Compositions which have a high SPF but do not compromise on cosmetic properties, such as greasy finish, tack and/or whitening, are sought.

The inventors have found, surprisingly, that compositions comprising UV-screening agents, a particular acrylic polymer and a dextrin ester make it possible to obtain stable compositions which have a high SPF and improved cosmetic properties. In particular, after application to the skin, there is no whitening effect, and the skin is neither greasy nor tacky.

The invention relates to a composition, especially a cosmetic composition, in particular a photoprotective composition, comprising at least:

a) one or more polymers comprising monomer units of formulae (A) and (B):

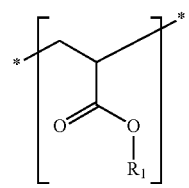

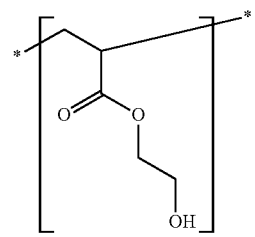

in which:
$R_1$, independently of one another, is chosen from alkyl or alkylene radicals,
and
at least 60% by weight of the $R_1$ groups are behenyl radicals, the percentage by weight relating to the sum of all the $R_1$ groups present in the polymer,
and
the weight ratio of the sum of all the hydroxyethyl acrylate units to the sum of all the acrylate units bearing the $R_1$ group ranges from 1:30 to 1:1;
and the sum of the total of units A and B is at least 95% by weight of the total weight of the polymer,
the polymer having a number-average molecular weight Mn ranging from 2000 to 9000 g/mol,
b) one or more fatty acid esters of dextrin, and
c) one or more UV-screening agents.

According to another of its aspects, the invention relates to a composition, especially a cosmetic, in particular photoprotective, composition, comprising, in a physiologically acceptable medium, a composition according to the invention as defined above.

The photoprotective cosmetic composition according to the invention is particularly suitable for performing a non-therapeutic process for the photoprotection of keratin materials.

The photoprotective cosmetic composition according to the invention has, for example, an SPF of at least 5, or even of at least 10, better still 15, better still at least 30, 45 or 60. The SPF (sunscreen protection factor) is defined in the article *A new substrate to measure sunscreen protection factors throughout the ultraviolet spectrum*, J. Soc. Cosmet. Chem., 40, 127-133 (May/June 1989).

The formulation of the photoprotective cosmetic composition is for example chosen such that the composition has a transmission factor less than or equal to 70%, 60%, 50%, 40%, 30%, 20%, 10%, 5% or best 1%, for at least one wavelength in the range 250-400 nm, better for the entirety of this range. The filtration is all the better when the transmission factor is low, in the range 250-400 nm.

According to another of its aspects, the invention relates to a non-therapeutic process for the photoprotection of keratin materials with respect to solar UV radiation, comprising a step of applying a cosmetic composition according to the invention to said keratin materials.

The invention also relates to a process for dyeing and/or lightening keratin materials, and to a process for modifying the spectral reflectance of keratin materials, each of these processes comprising a step of applying a cosmetic composition according to the invention to said keratin materials.

The invention also relates to a non-therapeutic cosmetic process for limiting the darkening of the skin and/or improving the colour and/or uniformity of the complexion, comprising a step of applying a cosmetic composition according to the invention to the skin.

The invention also relates to a non-therapeutic cosmetic process for preventing and/or treating the signs of ageing of a keratin material, comprising a step of applying a cosmetic composition according to the invention to the surface of said keratin material.

In the text hereinbelow, and unless otherwise indicated, the limits of a range of values are included within that range, especially in the expressions "between . . . and . . . " and "ranging from . . . to . . . ".

Moreover, the expressions "one or more" and "greater than or equal to" used in the present description are equivalent to the expressions "at least one" and "at least", respectively.

Fatty Acid Ester of Dextrin

The compositions according to the invention comprise at least one fatty acid ester, preferably $C_8$-$C_{30}$ fatty acid ester, of dextrin.

More particularly, the fatty acid ester of dextrin corresponds to formula (I):

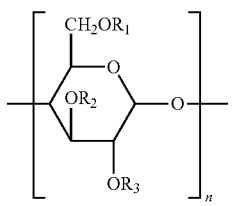

(I)

in which:
the radicals $R_1$, $R_2$ and $R_3$, which may be identical or different, are chosen from hydrogen or an acyl group (R—CO—) in which the radical R is a linear or branched, saturated or unsaturated hydrocarbon-based group containing from 6 to 30, especially from 8 to 22, or even 12-18 carbon atoms, with the proviso that at least one of said radicals $R_1$, $R_2$ or $R_3$ is other than hydrogen,
n is an integer between 3 and 150, especially 10 and 100 and preferably 15-40.

Preferably, the three radicals $R_1$, $R_2$ and $R_3$ are other than hydrogen, thereby resulting in dextrin esters having formula (II) below:

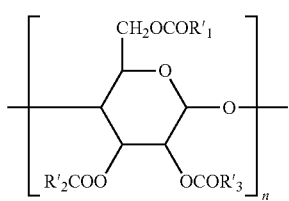

(II)

in which the radicals $R'_1$, $R'_2$ and $R'_3$, which may be identical or different, represent a linear or branched, saturated or unsaturated, hydrocarbon-based group having 6 to 30, especially 8 to 22, more particularly 12-18 carbon atoms,—n is an integer between 3 and 150, especially 10 and 100, and preferably 15-40.

In particular, the radicals —OCOR'$_1$, —OCOR'$_2$ and/or —OCOR'$_3$ may be chosen from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, a dextrin palmitate or a dextrin myristate is used.

Some of these dextrin esters are commercially available, especially under the name Rheopearl from the company Chiba Flour Milling Co.

These dextrin esters may be present in the composition according to the invention in an amount ranging from 0.1% to 10%, preferably from 0.2% to 5% by weight and more preferentially from 0.5% to 4% by weight, relative to the total weight of the composition.

Acrylic Polymer

The composition in accordance with the invention comprises at least one polymer a) comprising monomer units of formulae (A) and (B):

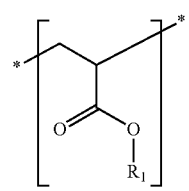

(A)

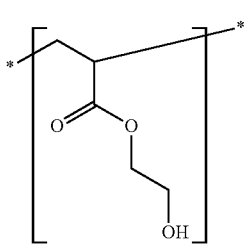

(B)

in which:
$R_1$, independently of one another, is chosen from alkyl and alkylene radicals,
and
at least 60% by weight of the $R_1$ groups are behenyl radicals, the weight percentage relating to the sum of all the $R_1$ groups present in the polymer,
and
the weight ratio of the sum of all the hydroxyethyl acrylate units to the sum of all the acrylate units bearing the $R_1$ group ranges from 1:30 to 1:1,
and the sum of the total of units A and B is at least 95% by weight of the total weight of the polymer.

Preferably, $R_1$ is constituted of alkyl radicals, preferably of $C_{16}$-$C_{22}$ alkyl radicals, and more preferentially of behenyl ($C_{22}$) radicals.

Preferably, at least 70% by weight of the $R_1$ groups are behenyl radicals, preferentially at least 80% by weight, more preferentially at least 90% by weight.

According to a preferred embodiment, all the $R_1$ groups are behenyl radicals.

Preferably, said weight ratio ranges from 1:15 to 1:1, preferentially ranges from 1:10 to 1:4.

Advantageously, the polymer units present in the polymer a) are constituted of the units (A) and (B) previously described.

The polymer a) has a number-average molecular weight Mn ranging from 2000 to 9000 g/mol, preferably ranging from 5000 to 9000 g/mol. The number-average molecular weight can be measured by the gel permeation chromatography method, for example according to the method described in the example hereinbelow.

Preferably, the polymer a) has a melting point ranging from 60° C. to 69° C., and preferentially ranging from 63° C. to 67° C. The melting point is measured by differential scanning calorimetry (DSC), for example according to the method described in the example hereinbelow.

The polymer a) used according to the invention can be prepared by polymerization of a monomer of formula

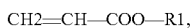

$R_1$ having the meaning previously described, and of 2-hydroxyethyl acrylate.

The polymerization may be performed according to known methods, such as solution polymerization or emulsion polymerization.

The polymerization is, for example, described in US 2007/0264204.

The polymer(s) a) according to the invention are preferably present in the composition in accordance with the invention in an amount ranging from 0.01% to 10% by weight, especially from 0.05% to 5% by weight and in particular from 0.1% to 3% by weight relative to the total weight of the composition.

UV-Screening Agents

The composition in accordance with the invention also comprises at least one UV-screening agent (agent for screening out UV radiation from sunlight). The UV-screening agent(s) can be chosen from organic UV-screening agents and inorganic UV-screening agents, which are hydrophilic, lipophilic or insoluble.

The term "UV-screening agent" is intended to mean a substance that is capable of absorbing at least a portion of the UV radiation emitted by the sun, to protect the skin and/or the lips and/or the hair against the harmful effects of this radiation. The UV-screening agent is a UV-screening agent normally used in cosmetics. It may be chosen from the positive list contained in Annex VI of (EC) Regulation No. 1223/2009, which specifies the list of UV-screening agents permitted in cosmetics.

According to a particular embodiment, the UV-screening agent(s) are present in the compositions according to the invention in an active material content ranging from 0.1% to 60% by weight and in particular from 5% to 45% by weight, relative to the total weight of the composition.

The water-soluble organic UV-screening agents are especially chosen from the following families:

Water-Soluble Screening Agents Capable of Absorbing UV Rays from 320 to 400 nm (UVA)

Terephthalylidenecamphor sulfonic acid manufactured under the name Mexoryl SX by Chimex.

Bis-benzazolyl derivatives as described in EP 669 323 and U.S. Pat. No. 2,463,264, and more particularly the compound disodium phenyldibenzimidazole tetrasulfonate sold under the trade name Neo Heliopan AP by Haarmann & Reimer.

The preferred screening agent is terephthalylidenecamphor sulfonic acid.

Water-Soluble Screening Agents Capable of Absorbing UV Rays from 280 to 320 nm (UVB)

p-Aminobenzoic acid (PABA) derivatives

PABA,

Glyceryl PABA and

PEG-25 PABA sold under the name Uvinul P25 by BASF,

Phenylbenzimidazole sulfonic acid sold especially under the trade name Eusolex 232 by Merck, Ferulic acid, Salicylic acid, DEA methoxycinnamate, Benzylidenecamphorsulfonic acid manufactured under the name Mexoryl SL by Chimex, Camphorbenzalkonium methosulfate manufactured under the name Mexoryl SO by Chimex, and, the preferred screening agent is phenylbenzimidazole sulfonic acid.

Mixed UVA and UVB Water-Soluble Screening Agents

Benzophenone derivatives comprising at least one sulfonic radical

Benzophenone-4, sold under the trade name Uvinul MS40 by BASF,

Benzophenone-5, and

Benzophenone-9.

When the absorber is an organic UV-screening agent of sulfonic acid type, it is preferably combined with an amount of an organic base, such as an alkanolamine, in such a way as to make it water-soluble.

The term "alkanolamine" is intended to mean a 02-010 compound comprising at least one primary, secondary or tertiary amine function and at least one alcohol, generally primary alcohol, function.

By way of suitable alkanolamine, mention may be made of tromethanine and triethanolamine.

The organic screening agents which are hydrophobic or insoluble in the usual solvents can in particular be chosen from various families of chemical compounds.

Hydrophobic screening agents capable of absorbing UV rays from 320 to 400 nm (UVA)

Dibenzoylmethane Derivatives

Butyl methoxydibenzoylmethane sold especially under the trade name Parsol 1789 by DSM Nutritional Products, Inc., Isopropyldibenzoylmethane.

Aminobenzophenones n-Hexyl 2-(4-diethylamino-2-hydroxybenzoyl)benzoate, sold under the trade name Uvinul A+ by BASF.

Anthranilic Derivatives

Menthyl anthranilate sold under the trade name Neo Heliopan MA by Symrise.

4,4-Diarylbutadiene Derivatives 1,1-Dicarboxy(2,2'-dimethylpropyl)-4,4-diphenylbutadiene.

The preferential screening agents are butyl methoxydibenzoylmethane and n-hexyl 2-(4-diethylamino-2-hydroxybenzoyl)benzoate.

Hydrophobic Screening Agents Capable of Absorbing UV Rays from 280 to 320 nm (UVB)

Para-Aminobenzoates

Ethyl PABA,

Ethyl dihydroxypropyl PABA,

Ethylhexyl dimethyl PABA (Escalol 507 from ISP).

Salicylic Derivatives
Homosalate sold under the name Eusolex HMS by Rona/EM Industries,
Ethylhexyl salicylate sold under the name Neo Heliopan OS by Symrise,
Dipropylene glycol salicylate sold under the name Dipsal by Scher,
TEA salicylate sold under the name Neo Heliopan TS by Symrise.

Cinnamates
Ethylhexyl methoxycinnamate sold in particular under the trade name Parsol MCX by DSM Nutritional Products, Inc.,
Isopropyl methoxycinnamate,
Isoamyl methoxycinnamate sold under the trade name Neo Heliopan E 1000 by Symrise,
Diisopropyl methylcinnamate,
Cinoxate,
Glyceryl ethylhexanoate dimethoxycinnamate.

β,β'-Diphenylacrylate derivatives
Octocrylene sold especially under the trade name Uvinul N539 by BASF,
Etocrylene sold in particular under the trade name Uvinul N35 by BASF.

Benzylidenecamphor Derivatives
3-Benzylidenecamphor manufactured under the name Mexoryl SD by Chimex,
Methyl benzylidenecamphor sold under the name Eusolex 6300 by Merck,
Polyacrylamidomethylbenzylidenecamphor manufactured under the name Mexoryl SW by Chimex.

Triazine Derivatives
Ethylhexyltriazone sold especially under the trade name Uvinul T150 by BASF,
Diethylhexyl butamido triazone sold under the trade name Uvasorb HEB by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-bis(dineopentyl 4'-aminobenzalmalonate)-6-(n-butyl 4'-aminobenzoate)-s-triazine,
2,4-bis(n-butyl 4'-aminobenzoate)-6-(aminopropyltrisiloxane)-s-triazine,
the symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc West Henrietta, N.Y., USA (20 Sep. 2004) in particular 2,4,6-tris-(diphenyl)-1,3,5-triazines (in particular 2,4,6-tris(diphenyl-4-yl-1,3,5-triazine)) and 2,4,6-tris(terphenyl)-1,3,5-triazine, which is reiterated in the Beiersdorf applications WO 06/035000, WO 06/034982, WO 06/034991, WO 06/035007, WO 2006/034992, WO 2006/034985.

Imidazoline Derivatives
Ethylhexyl dimethoxybenzylidene dioxoimidazoline propionate.

Benzalmalonate Derivatives
Polyorganosiloxanes containing benzalmalonate functions, for instance Polysilicone-15, sold under the trade name Parsol SLX by DSM Nutritional Products, Inc.,
Dineopentyl 4'-methoxybenzalmalonate.

Merocyanine Derivatives
Octyl-5-N,N-diethylamino-2-phenysulfonyl-2,4-pentadienoate.

The preferred screening agents are homosalate, ethylhexylsalicylate, octocrylene, ethylhexyl, methoxycinnamate v, isoamyl methoxycinnamate, ethylhexyl triazone, diethylhexyl butamido triazone.

The most preferential are ethylhexyl salicylate, octocrylene, ethylhexyl triazone, and ethylhexyl methoxycinnamate.

Mixed Hydrophobic Screening Agents Capable of Absorbing Both UVA and UVB Rays

Benzophenone Derivatives
Benzophenone-1 sold under the trade name Uvinul 400 by BASF,
Benzophenone-2 sold under the trade name Uvinul D50 by BASF,
Benzophenone-3 or oxybenzone sold under the trade name Uvinul M40 by BASF,
Benzophenone-5,
Benzophenone-6 sold under the trade name Helisorb 11 by Norquay,
Benzophenone-8 sold under the trade name Spectra-Sorb UV-24 by American Cyanamid,
Benzophenone-10,
Benzophenone-11,
Benzophenone-12.

Phenylbenzotriazole Derivatives
Drometrizole trisiloxane sold under the name Silatrizole by Rhodia Chimie, methylenebis(benzotriazolyl)tetramethylbutylphenol sold in solid form under the trade name MIXXIM BB/100 by Fairmount Chemical, or in micronized form as an aqueous dispersion under the trade name Tinosorb M by Ciba Specialty Chemicals.

Bis-Resorcinyl Triazine Derivatives
Bis(ethylhexyloxyphenol)methoxyphenyltriazine sold under the trade name Tinosorb S by Ciba Geigy.

Benzoxazole Derivatives
2,4-Bis[5-1(dimethylpropyl)benzoxazol-2-yl-(4-phenyl)imino]-6-(2-ethylhexyl)imino-1,3,5-triazine sold under the name Uvasorb K2A by Sigma 3V.

The preferential screening agents are:
Drometrizole trisiloxane,
Methylenebis(benzotriazolyl) tetramethylbutylphenol,
Bis(ethylhexyloxyphenol)methoxyphenyltriazine, and
Benzophenone-3 or Oxybenzone.

The most preferential screening agents are:
Drometrizole trisiloxane, and
Bis(ethylhexyloxyphenol)methoxyphenyltriazine.

Mention may also be made of the merocyanine-type screening agents in particular prepared according to the protocols described in WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 (col. 13, 1.66 col. 14, 1.57 and the references cited in this regard).

Inorganic Anti-Sun or Photoprotective Screening Agents

The inorganic photoprotective agents are chosen from coated or uncoated metal oxide pigments (mean size of the primary particles: generally between 5 nm and 100 nm, preferably between 10 nm and 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may or may not be coated.

The coated pigments are pigments that have undergone one or more surface treatments of chemical, electronic, mechanochemical and/or mechanical nature with compounds as described, for example, in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

In a known manner, silicones are organosilicon polymers or oligomers comprising a linear or cyclic and branched or crosslinked structure, of variable molecular weight, obtained by polymerization and/or polycondensation of suitably functionalized silanes and essentially constituted of a repetition of main units in which the silicon atoms are connected to one another via oxygen atoms (siloxane bond), optionally substituted hydrocarbon-based radicals being connected directly to said silicon atoms via a carbon atom.

The term "silicones" also encompasses the silanes necessary for their preparation, in particular alkylsilanes.

The silicones used for coating the pigments that are suitable for the present invention are preferably chosen from the group containing alkylsilanes, polydialkylsiloxanes and polyalkylhydrosiloxanes. Even more preferentially, the silicones are chosen from the group containing octyltrimethylsilane, polydimethylsiloxanes and polymethylhydrosiloxanes.

Of course, the pigments of metal oxides may, before their treatment with silicones, have been treated with other surfacing agents, in particular with cerium oxide, alumina, silica, aluminium compounds, silicon compounds or mixtures thereof.

The coated pigments are more particularly titanium oxides that have been coated:
  with silica, such as the product Sunveil from the company Ikeda,
  with silica and iron oxide, such as the product Sunveil F from the company Ikeda,
  with silica and alumina, such as the products Microtitanium Dioxide MT 500 SA and Microtitanium Dioxide MT 100 SA from the company Tayca and Tioveil from the company Tioxide,
  with alumina, such as the products Tipaque TTO-55 (B) and Tipaque TTO-55 (A) from the company Ishihara and UVT 14/4 from the company Kemira,
  with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
  with silica, alumina and alginic acid, such as the product MT-100 AQ from the company Tayca,
  with alumina and aluminium laurate, such as the product Microtitanium Dioxide MT 100 S from the company Tayca,
  with iron oxide and iron stearate, such as the product Microtitanium Dioxide MT 100 F from the company Tayca,
  with zinc oxide and zinc stearate, such as the product BR 351 from the company Tayca,
  with silica and alumina and treated with a silicone, such as the products Microtitanium Dioxide MT 600 SAS, Microtitanium Dioxide MT 500 SAS or Microtitanium Dioxide MT 100 SAS from the company Tayca,
  with silica, alumina and aluminium stearate and treated with a silicone, such as the product STT-30-DS from the company Titan Kogyo,
  with silica and treated with a silicone, such as the product UV-Titan X 195 from the company Kemira,
  with alumina and treated with a silicone, such as the products Tipaque TTO-55 (S) from the company Ishihara or UV Titan M 262 from the company Kemira,
  with triethanolamine, such as the product STT-65-S from the company Titan Kogyo,
  with stearic acid, such as the product Tipaque TTO-55 (C) from the company Ishihara,
  with sodium hexametaphosphate, such as the product Microtitanium Dioxide MT 150 W from the company Tayca,
  $TiO_2$ treated with octyltrimethylsilane, sold under the trade name T 805 by the company Degussa Silices,
  $TiO_2$ treated with a polydimethylsiloxane, sold under the trade name 70250 Cardre UF TiO2SI3 by the company Cardre, and
  anatase/rutile $TiO_2$ treated with a polydimethylhydrosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
  those sold under the name Z-Cote by the company Sunsmart,
  those sold under the name Nanox by the company Elementis,
  those sold under the name Nanogard WCD 2025 by the company Nanophase Technologies.

The coated zinc oxide pigments are, for example:
  those sold under the name Zinc Oxide CS-5 by the company Toshibi (ZnO coated with polymethylhydrosiloxane),
  those sold under the name Nanogard Zinc Oxide FN by the company Nanophase Technologies (as a 40% dispersion in Finsolv TN, $C_{12}$-$C_{15}$ alkyl benzoate),
  those sold under the name Daitopersion ZN-30 and Daitopersion ZN-50 by the company Daito (dispersions in cyclopolymethylsiloxane/oxyethylenated polydimethylsiloxane, containing 30% or 50% of nano zinc oxides coated with silica and polymethylhydrosiloxane),
  those sold under the name NFD Ultrafine ZnO by the company Daikin (ZnO coated with perfluoroalkyl phosphate and copolymer based on perfluoroalkylethyl as a dispersion in cyclopentasiloxane),
  those sold under the name SPD-Z1 by the company Shin-Etsu (ZnO coated with silicone-grafted acrylic polymer, dispersed in cyclodimethylsiloxane),
  those sold under the name Escalol Z100 by the company ISP (alumina-treated ZnO dispersed in an ethylhexyl methoxycinnamate/PVP-hexadecene/methicone copolymer mixture),
  those sold under the name Fuji ZnO-SMS-10 by the company Fuji Pigment (ZnO coated with silica and polymethylsilsesquioxane),
  those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments are sold under the name Colloidal Cerium Oxide by the company Rhône-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

The inorganic screening agent(s) may be present in the compositions according to the invention in a concentration of between 0.1% and 15% and preferably between 0.2% and 10% by weight relative to the total weight of the composition.

Preferably, the weight ratio of the dextrin ester to the polymer a) is between 0.1 and 10, preferably from 0.25 to 4.

The composition of the invention comprises an aqueous phase.

The term "aqueous phase" denotes a medium which is liquid at ambient temperature and atmospheric pressure and which contains a large fraction of water relative to the total weight of the medium. The weight content of water in the aqueous composition is preferably greater than or equal to 10%, advantageously greater than or equal to 30%, preferentially greater than equal to 40%, or even greater than 50%.

The composition may be single-phase or multi-phase.

The composition according to the invention may also contain at least one polar organic solvent, which is preferably physiologically acceptable.

The polar organic solvents are generally water-miscible.

As polar organic solvent, mention may be made of $C_1$-$C_6$ monoalcohols such as ethanol or isopropanol; $C_1$-06 polyols such as glycerol, 1,3-propanediol, 1,4-butanediol, 1,5-pentanediol and 1,6-hexanediol; $C_1$-$C_6$ alkylene glycols such as ethylene glycol, propylene glycol, dipropylene glycol, butylene glycol, pentylene glycol and hexylene glycol; and mixtures thereof.

The total content of $C_1$-06 alcohols in the composition of the invention is preferably from 0.1% to 10% by weight, preferentially from 1% to 5% by weight of $C_1$-06 alcohols relative to the total weight of the composition.

The total content of $C_1$-$C_6$ alkylene glycols in the composition of the invention is preferably from 0.1% to 30% by weight, preferentially from 5% to 25% by weight of $C_1$-$C_6$ alkylene glycols relative to the total weight of the composition.

The composition according to the invention may be transparent or translucent, and coloured or uncoloured. The composition according to the invention may contain no pigment or dye. The colouration may correspond to the addition of an additional colouring agent.

The composition according to the invention may comprise a volatile solvent.

For the purposes of the invention, the term "volatile solvent" is intended to mean any liquid that can evaporate on contact with keratin materials, at ambient temperature and under atmospheric pressure.

The composition according to the invention may in particular be chosen in such a way that the composition contains at least 5%, or even at least 30%, or even at least 40% of volatile solvent.

Fatty Phase

The composition according to the invention comprises a fatty phase.

The composition may include an oil such as for example synthetic esters and ethers, linear or branched hydrocarbons of mineral or synthetic origin, fatty alcohols having from 8 to 26 carbon atoms, partially hydrocarbon-based and/or silicone-based fluorinated oils, silicone oils such as volatile or non-volatile polymethylsiloxanes (PDMS) with linear or cyclic silicone chains, that are liquid or pasty at ambient temperature and mixtures thereof, other examples being given hereinafter.

A composition in accordance with the invention may thus comprise at least one volatile oil.

Volatile Oils

For the purposes of the present invention, the term "volatile oil" is intended to mean an oil (or non-aqueous medium) that is capable of evaporating on contact with the skin in less than one hour, at ambient temperature and at atmospheric pressure.

The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils of animal or plant origin containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, such as, for example, volatile linear or cyclic silicone oils, especially those having a viscosity 8 centistokes ($8 \times 10^{-6}$ m²/s), and especially having from 2 to 10 silicon atoms and in particular from 2 to 7 silicon atoms, these silicones optionally comprising alkyl or alkoxy groups having from 1 to 10 carbon atoms. As volatile silicone oil that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

Non-Volatile Oils

A composition according to the invention may comprise a non-volatile oil.

For the purposes of the present invention, the term "non-volatile oil" is intended to mean an oil with a vapour pressure of less than 0.13 Pa and especially oils of high molar mass.

The non-volatile oils may be chosen especially from non-volatile hydrocarbon-based oils, which may be fluorinated, and/or silicone oils.

As non-volatile hydrocarbon-based oil that may be suitable for the implementation of the invention, mention may be made especially of:

hydrocarbon-based oils of animal origin, hydrocarbon-based oils of plant origin such as phytostearyl esters, such as phytostearyl oleate, phytostearyl isostearate and lauroyl/octyl-dodecyl/phytostearyl glutamate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stéarinerie Dubois or those sold under the names Miglyol 810®, 812® and 818® by the company Dynamit Nobel, hydrocarbon-based oils of mineral or synthetic origin, for instance:

synthetic ethers containing from 10 to 40 carbon atoms, linear or branched hydrocarbons of mineral or synthetic origin, such as petroleum jelly, polydecenes, hydrogenated polyisobutene such as Parleam, and squalane, and mixtures thereof, and in particular hydrogenated polyisobutene, synthetic esters, such as the oils of formula $R_1COOR_2$, in which $R_1$ represents the residue of a linear or branched fatty acid including from 1 to 40 carbon atoms and $R_2$ represents an especially branched hydrocarbon-based chain containing from 1 to 40 carbon atoms, with the proviso that $R_1+R_2$ is $\geq 10$.

The esters may be chosen especially from especially fatty acid esters, for instance:

cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythritol tetrahydroxystearate/tetraisostearate, esters of diol dimers and of diacid dimers, such as Lusplan DD-DA5® and Lusplan DD-DA7® sold by the company Nippon Fine Chemical and described in patent application FR 0302809, fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol, higher fatty acids such as oleic acid, linoleic acid and linolenic acid, and mixtures thereof, and dialkyl carbonates, the two alkyl chains possibly being identical or different, such as the dicaprylyl carbonate sold under the name Cetiol CC® by Cognis, non-volatile silicone oils, for instance non-volatile polydimethylsiloxanes (PDMSs), polydimethylsiloxanes comprising alkyl or alkoxy groups that are on the side and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicone with a viscosity of less than or equal to 100 cSt, and mixtures thereof, and mixtures thereof.

Additives

The composition according to the invention may comprise at least one additive chosen from the adjuvants typical of the cosmetic domain, such as fillers, colouring agents, hydrophilic or lipophilic gellants, water-soluble or liposoluble active agents, preservatives, moisturizers such as polyols and especially glycerine, sequestrants, antioxidants, solvents, fragrances, odour absorbers, pH adjusters (acids or bases) and mixtures thereof.

The composition may contain at least one active agent which has a supplementary activity in the solar protection field, such as antioxidants, whitening agents in the context of anti-pigmentation and depigmentation, and anti-ageing active agents.

The additive or additives may be chosen from those cited in the CTFA Cosmetic Ingredient Handbook, 10th Edition Cosmetic and Fragrance Assn, Inc., Washington D.C. (2004), incorporated here by reference.

Presentation Forms

The composition according to the invention may be a lotion, a two-phase composition, a cream, a milk, an ointment or a gel, for the skin, the lips, the hair or the nails.

Photoprotective Cosmetic Composition

According to another of its aspects, the invention relates to a photoprotective cosmetic composition comprising, in a physiologically acceptable medium, a composition according to the invention as defined above.

The term "physiologically acceptable medium" is intended to mean a non-toxic medium that may be applied to keratin materials, in particular the skin, mucous membranes and appendages.

This medium is adapted to the nature of the support onto which the composition is to be applied, and also to the form in which the composition is intended to be packaged.

The composition may be packaged in any packaging device, in particular made of thermoplastic, or on any support intended for this purpose.

The packaging device may be a bottle, a pump-dispenser bottle, an aerosol container, a tube, a sachet or a pot.

Cosmetic Non-Therapeutic Photoprotection Process

The photoprotective cosmetic composition may be applied by hand or using an applicator.

The application may also be carried out by spraying or projection using, for example, a piezoelectric or aerograph device or by transfer of a layer of composition previously deposited on an intermediate support.

EXAMPLES

Example of Preparation of Polymer 1

Determination of the Molecular Weight by Gel Permeation Chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes to aid dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 μm nylon filter, before being injected into the liquid chromatograph. The standards used for the calibration are the Easi Vial narrow polystyrene (PS) standards from Agilent Technologies.

Polystyrene standards ranging from 2 520 000 to 162 daltons were used for the calibration.

The system is equipped with a PSS SECcurity 1260 RI detector. The polystyrene calibration curve was used to determine the average molecular weight. The recording of the diagrams and the determination of the various molecular weights were performed by the Win GPC Unichrom 81 program.

Determination of the Melting Point by Differential Scanning Calorimetry (or DSC):

This method describes the general procedure for determining the melting point of polymers by differential scanning calorimetry. This method is based on the standards ASTM E791 and ASTM D 34182 and the DSC calibration is performed according to standard ASTM E 9672.

Behenyl Acrylate/2-Hydroxyethyl Acrylate Copolymer (Polymer 1):

In a 4-necked flask equipped with side-blade mixer, an internal thermometer, two funnels, a reflux condenser, and an extension for two other necks, 175 g of behenyl acrylate, 25 g of 2-hydroxyethyl acrylate and 0.4 g of 2,2'-azobis(2-methylbutyronitrile) (Akzo Nobel) were added, over the course of 60 minutes at 80° C., to 40 g of isopropanol, with stirring, after having removed the oxygen from the system by means of a nitrogen flush for 20 minutes. The mixture was stirred at 80° C. for 3 hours. The solvent was then eliminated by vacuum distillation, then 1 g of dilauryl peroxide was added and the reaction was continued for 60 minutes at 110° C. The step was repeated. The mixture was then cooled to 90° C., a stream of demineralized water was added and the mixture was then stirred. The water was removed by vacuum distillation.

Molecular weight: Mn=7300 g/mol, Mw=21 000, Mw/Mn=2.8

Melting point: 65° C.

Examples 1 to 4

The following O/W emulsions were prepared:

| Phase | INCI name | 1 (invention) | 2 | 3 | 4 |
|---|---|---|---|---|---|
| A | BIS-ETHYLHEXYLOXYPHENOL METHOXYPHENYL TRIAZINE | 3.00 | 3.00 | 3.00 | 3.00 |
|  | DROMETRIZOLE TRISILOXANE (MEXORYL XL) | 2.00 | 2.00 | 2.00 | 2.00 |
|  | HOMOSALATE | 8.00 | 8.00 | 8.00 | 8.00 |
|  | OCTYL SALICILATE | 5.00 | 5.00 | 5.00 | 5.00 |
|  | DIETHYLAMINO HYDROXYBENZOYL HEXYL BENZOATE | 3.00 | 3.00 | 3.00 | 3.00 |
|  | OCTOCRYLENE | 1.50 | 1.50 | 1.50 | 1.50 |
|  | DICAPRYLYL CARBONATE | 3.00 | 3.00 | 3.00 | 3.00 |
|  | DIISOPROPYL SEBACATE | 3.00 | 3.00 | 3.00 | 3.00 |
|  | ISOHEXADECANE | 2.00 | 2.00 | 2.00 | 2.00 |
|  | ISOPROPYL LAUROYL SARCOSINATE | 4.00 | 4.00 | 4.00 | 4.00 |
|  | BEHENYL ALCOHOL (and) GLYCERYL STEARATE (and) DISODIUM ETHYLENE DICOCAMIDE PEG-15 DISULFATE (and) GLYCERYL STEARATE CITRATE (CERALUTION H from SASOL) | 2.00 | 2.00 | 2.00 | 2.00 |
|  | DEXTRIN PALMITATE (RHEOPEARL from CHIBA FLOUR MILLING) | 2.00 |  |  | 5.00 |
|  | ETHYLENEDIAMINE/STEARYL DIMER DILINOLEATE COPOLYMER |  |  | 2.00 |  |
|  | Polymer 1 | 3.00 | 3.00 |  | 5.00 |
| B | GLYCEROL | 5.00 | 5.00 | 5.00 | 5.00 |
|  | CAPRYLYL GLYCOL | 0.50 | 0.50 | 0.50 | 0.50 |
|  | PHENYLBENZIMIDAZOLE SULFONIC ACID | 2.00 | 2.00 | 2.00 | 2.00 |

-continued

| Phase | INCI name | 1 (invention) | 2 | 3 | 4 |
|---|---|---|---|---|---|
| | TROMETHAMINE | 1.80 | 1.80 | 1.80 | 1.80 |
| | XANTHAN GUM | 0.50 | 0.50 | 0.50 | 0.50 |
| | WATER | qs 100 | qs 100 | qs 100 | qs 100 |
| C | DENAT. ALCOHOL | 5.00 | 5.00 | 5.00 | 5.00 |
| | Stability (2 months at 45° C.) | OK | OK | OK | OK |
| | Stability (2 months at 4° C.) | OK | OK | OK | Crystal formation |
| | in vitro SPF | 65.8 +/− 2.4 | 41.8 +/− 3.5 | 43.5 +/− 3.1 | 41.8 +/− 4.7 |
| | Non-greasy finish (Score by sensory expert panel, out of 15; 1 = Greasy finish; 15 = Non-greasy finish) | 12.8 +/− 1.3 | 5.1 +/− 1.4 | 6.8 +/− 0.2 | 5.1 +/− 1.5 |

Protocol for Evaluating the Greasy Finish

The greasy finish is evaluated by a panel of sensory experts made up of 10 individuals. Each composition is applied to the forearm at a dose of 2 mg/cm². The product is spread by circular movements until it had penetrated (approximately 30 seconds). The evaluation of the greasy finish is carried out after 2 minutes of drying, according to a scale ranging from 1 to 15 where 1 constitutes a non-greasy finish reference (bare skin) and 15 constitutes a very greasy finish reference.

In Vitro SPF

The sun protection factor (SPF) is determined according to the "in vitro" method described by B. L. Diffey in J. Soc. Cosmet. Chem. 40, 127-133, (1989). The measurements were taken by means of a UV-2000S spectrophotometer from the company Labsphere. Each composition is applied to a rough plate of PMMA, in the form of a uniform and even deposit in a proportion of 1.3 mg/cm².

Preparation Method

The starting materials are first weighed out carefully using a balance (precision=0.01 g).

- The components of phase A are heated to 70° C. using a hotplate, and are mixed using a Rayneri blender.
- Phase B is heated to 70° C. and then introduced into phase A. The emulsification is carried out at 70° C. using a rotor-stator of Moritz type. After 10 minutes of emulsion, the preparation is brought back to ambient temperature.
- Phase C is introduced into the emulsion A+B with Rayneri stirring at ambient temperature.

The composition according to the invention has a high SPF while at the same time having a non-greasy finish after application.

Examples 5 and 6

O/W emulsions according to the invention were prepared.

| Phase | INCI name | 5 (invention) | 6 (invention) |
|---|---|---|---|
| A | BIS-ETHYLHEXYLOXYPHENOL METHOXYPHENYL TRIAZINE | 3.00 | 3.00 |
| | DROMETRIZOLE TRISILOXANE (MEXORYL XL) | 2.00 | 2.00 |
| | HOMOSALATE | 8.00 | 8.00 |
| | OCTYL SALICILATE | 5.00 | 5.00 |
| | DIETHYLAMINO HYDROXYBENZOYL HEXYL BENZOATE | 3.00 | 3.00 |
| | OCTOCRYLENE | 1.50 | 1.50 |
| | DICAPRYLYL CARBONATE | 3.00 | 3.00 |
| | DIISOPROPYL SEBACATE | 3.00 | 3.00 |
| | ISOHEXADECANE | 2.00 | 2.00 |
| | ISOPROPYL LAUROYL SARCOSINATE | 4.00 | 4.00 |
| | BEHENYL ALCOHOL (and) GLYCERYL STEARATE (and) DISODIUM ETHYLENE DICOCAMIDE PEG-15 DISULFATE (and) GLYCERYL STEARATE CITRATE (CERALUTION H from SASOL) | 2.00 | 2.00 |
| | Polymer 1 | 3.00 | 3.00 |
| | DEXTRIN PALMITATE (RHEOPEARL from CHIBA FLOUR MILLING) | 1.00 | 3.00 |
| B | GLYCEROL | 5.00 | 5.00 |
| | CAPRYLYL GLYCOL | 0.50 | 0.50 |
| | PHENYLBENZIMIDAZOLE SULFONIC ACID | 2.00 | 2.00 |
| | TROMETHAMINE | 1.80 | 1.80 |
| | XANTHAN GUM | 0.50 | 0.50 |
| | WATER | qs 100% | qs 100% |
| C | DENAT. ALCOHOL | 5.00 | 5.00 |
| | Stability (2 months at 45° C.) | OK | OK |
| | Stability (2 months at 4° C.) | OK | OK |
| | in vitro SPF | 59.0 ± 4.6 | 67.4 ± 4.1 |
| | Non-greasy finish (Score by sensory expert panel, out of 15; 1 = Greasy finish; 15 = Non-greasy finish) | 12.1 ± 1.7 | 13.5 ± 1.4 |

Preparation Method

The starting materials are first weighed out carefully using a balance (precision=0.01 g).

- The components of phase A are heated to 70° C. using a hotplate, and are mixed using a Rayneri blender.
- Phase B is heated to 70° C. and then introduced into phase A. The emulsification is carried out at 70° C. using a rotor-stator of Moritz type. After 10 minutes of emulsion, the preparation is brought back to ambient temperature.
- Phase C is introduced into the emulsion A+B with Rayneri stirring at ambient temperature.

Examples 7 and 8

W/O emulsions according to the invention were prepared.

| Phase | INCI name | 7 (invention) | 8 (invention) |
|---|---|---|---|
| A | BIS-ETHYLHEXYLOXYPHENOL METHOXYPHENYL TRIAZINE | 3.00 | 3.00 |
|  | DROMETRIZOLE TRISILOXANE (MEXORYL XL) | 2.00 | 2.00 |
|  | HOMOSALATE | 8.00 | 8.00 |
|  | OCTYL SALICILATE | 5.00 | 5.00 |
|  | DIETHYLAMINO HYDROXYBENZOYL HEXYL BENZOATE | 3.00 | 3.00 |
|  | OCTOCRYLENE | 1.50 | 1.50 |
|  | DICAPRYLYL CARBONATE | 3.00 | 3.00 |
|  | DIISOPROPYL SEBACATE | 6.00 | 6.00 |
|  | ISOHEXADECANE | 4.00 | 6.00 |
|  | ISOPROPYL LAUROYL SARCOSINATE | 8.00 | 8.00 |
|  | PEG-30 DIPOLYHYDROXYSTEARATE | 2.00 | 2.00 |
|  | Polymer 1 | 1.00 | 2.00 |
|  | DEXTRIN PALMITATE (RHEOPEARL from CHIBA FLOUR MILLING) | 1.00 | 1.00 |
| B | GLYCEROL | 5.00 | 5.00 |
|  | CAPRYLYL GLYCOL | 0.50 | 0.50 |
|  | PHENYLBENZIMIDAZOLE SULFONIC ACID | 2.00 | 2.00 |
|  | TROMETHAMINE | 1.80 | 1.80 |
|  | XANTHAN GUM | 0.50 | 0.50 |
|  | SODIUM CHLORIDE | 0.5 | 0.5 |
|  | WATER | qs 100 | qs 100 |
|  | Stability (2 months at 45° C.) | OK | OK |
|  | Stability (2 months at 4° C.) | OK | OK |

Preparation Method

The starting materials are first weighed out carefully using a balance

The components of phase A are heated to 70° C. using a hotplate, and are mixed using a Rayneri blender.

Phase B is heated to 70° C. and then introduced into phase A. The emulsification is carried out at 70° C. using a rotor-stator of Moritz type. After 10 minutes of emulsion, the preparation is brought back to ambient temperature.

The invention claimed is:

1. A composition comprising at least:

a) 0.01% to 10% by weight, relative to the total weight of the composition of one or more polymers comprising monomer units of formulae (A) and (B):

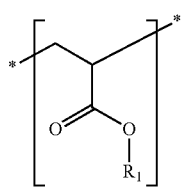

(A)

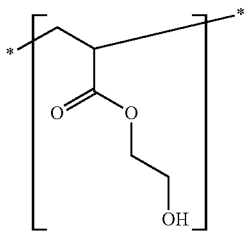

(B)

in which:
$R_1$, independently of one another, is chosen from alkyl or alkylene radicals,
and
at least 60% by weight of the $R_1$ groups are behenyl radicals, the percentage by weight relating to the sum of all the $R_1$ groups present in the polymer,
and
the weight ratio of the sum of all the hydroxyethyl acrylate units to the sum of all the acrylate units bearing the $R_1$ group ranges from 1:30 to 1:1;
and the sum of the total of units A and B is at least 95% by weight of the total weight of the polymer,
the polymer having a number-average molecular weight Mn ranging from 2000 to 9000 g/mol, b) from 0.1% to 10% relative to the total weight of said composition of one or more fatty acid esters of dextrin, and c) 0.01% to 60% by weight, relative to the total weight of said composition of one or more UV-screening agents.

2. The composition according to claim 1, in which the fatty acid ester of dextrin corresponds to formula (I):

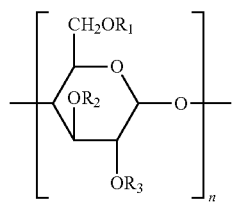

(I)

in which:
the radicals $R_1$, $R_2$ and $R_3$, which may be identical or different, are chosen from hydrogen or an acyl group (R—CO—) in which the radical R is a linear or branched, saturated or unsaturated hydrocarbon-based group containing from 6 to 30 with the proviso that at least one of said radicals $R_1$, $R_2$ or $R_3$ is other than hydrogen,
n is an integer between 3 and 150.

3. The composition according to claim 2, in which the weight content of fatty acid ester of dextrin is from 0.2% to 5% by weight relative to the total weight of the composition.

4. The composition according to claim 2, in which the one or more UV-screening agents are chosen from soluble or insoluble organic UV-screening agents, mineral UV-screening agents, and mixtures thereof.

5. The composition according to claim 1, in which the fatty acid ester of dextrin is chosen from dextrin palmitate and dextrin myristate, and mixtures thereof.

6. The composition according to claim 5, in which the weight content of fatty acid ester of dextrin is from 0.2% to 5% by weight relative to the total weight of the composition.

7. The composition according to claim 1, in which the weight content of fatty acid ester of dextrin is from 0.2% to 5% by weight relative to the total weight of the composition.

8. The composition according to claim 1, in which the one or more UV-screening agents are chosen from soluble or insoluble organic UV-screening agents, mineral UV-screening agents, and mixtures thereof.

9. The composition according to claim 1, in which the content of the one or more UV-screening agents is from 5% to 45% by weight, relative to the total weight of said composition.

10. The composition according to claim 1, in which, in the polymer a), $R_1$ is constituted of an alkyl radical.

11. The composition according to claim 1, in which, in the polymer a), at least 70% by weight of the $R_1$ groups are behenyl radicals.

12. The composition according to claim 1, in which, in the polymer a), all the $R_1$ groups are behenyl radicals.

13. The composition according to claim 1, in which, in the polymer a), said weight ratio of the sum of all the hydroxyethyl acrylate units to the sum of all the acrylate units bearing the $R_1$ group ranges from 1:15 to 1:1.

14. The composition according to claim 1, in which the polymer a) has a number-average molecular weight Mn ranging from 5000 to 9000 g/mol.

15. The composition according to claim 1, in which the polymer a) has a melting point ranging from 60° C. to 69° C.

16. The composition according to claim 1, in which the content of polymer a) is from 0.05% to 5% by weight, relative to the total weight of said composition.

17. The composition according to claim 1, also comprising at least one polar organic solvent.

18. The composition according to claim 1, wherein $R_1$, independently of one another, is chosen from $C_{16}$-$C_{22}$ alkyl radicals and the fatty acid ester of dextrin is chosen from dextrin palmitate and dextrin myristate, and mixtures thereof.

19. The composition according to claim 18 wherein in the polymer a), all the $R_1$ groups are behenyl radicals.

20. A non-therapeutic process for the photoprotection of keratin materials with respect to solar UV radiation, comprising a step of applying a composition according to claim 1 to said keratin materials.

21. A non-therapeutic cosmetic process for limiting the darkening of the skin and/or improving the colour and/or uniformity of the complexion, comprising a step of applying a composition according to claim 1.

22. A non-therapeutic cosmetic process for treating the signs of ageing of a keratin material, comprising a step of applying a composition according to claim 1 to the surface of said keratin material.

* * * * *